(12) United States Patent
Toida et al.

(10) Patent No.: US 6,522,911 B1
(45) Date of Patent: Feb. 18, 2003

(54) APPARATUS FOR IMAGING A BLOOD VESSEL

(75) Inventors: Masahiro Toida, Kaisei-machi (JP); Tomoo Sato, Kaisei-machi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/444,514

(22) Filed: Nov. 22, 1999

(30) Foreign Application Priority Data

Nov. 20, 1998 (JP) .......................................... 10-330763

(51) Int. Cl.⁷ ............................................... A61B 5/00
(52) U.S. Cl. ...................... 600/473; 600/476; 600/310; 356/319; 356/450; 356/484
(58) Field of Search ................................ 600/473, 475, 600/476, 322, 316, 310, 317, 323, 326, 330, 335, 336, 407; 356/319, 450, 484, 485

(56) References Cited

U.S. PATENT DOCUMENTS

| | | | | |
|---|---|---|---|---|
| 4,427,889 A | * | 1/1984 | Muller ........................ | 250/339 |
| 4,817,622 A | * | 4/1989 | Pennypacker et al. ...... | 250/330 |
| 5,101,825 A | * | 4/1992 | Gravenstein et al. ....... | 128/898 |
| 5,137,355 A | * | 8/1992 | Barbour et al. .......... | 356/237.1 |
| 5,277,181 A | * | 1/1994 | Mendelson et al. ......... | 128/633 |
| 5,553,615 A | * | 9/1996 | Carim et al. ................ | 128/633 |
| 5,673,701 A | * | 10/1997 | Chance ....................... | 600/473 |
| 5,676,143 A | * | 10/1997 | Simonsen et al. ............ | 356/39 |
| 5,769,076 A | * | 6/1998 | Maekawa et al. ........... | 600/322 |
| 5,934,278 A | * | 8/1999 | Ishihara et al. ................ | 356/39 |
| 5,947,906 A | * | 9/1999 | Dawson et al. ............. | 250/226 |
| 6,038,158 A | * | 3/2000 | Bessho et al. .............. | 365/190 |
| 6,061,583 A | * | 5/2000 | Ishihara et al. ............. | 600/322 |
| 6,063,093 A | * | 5/2000 | Winston et al. ............. | 600/117 |
| 6,094,592 A | * | 7/2000 | Yorkey et al. ............... | 600/475 |
| 6,104,939 A | * | 8/2000 | Groner et al. ............... | 356/364 |
| 6,230,046 B1 | * | 5/2001 | Crane et al. ................. | 250/330 |
| 6,240,309 B1 | * | 5/2001 | Yamashita et al. ........ | 250/227.2 |
| 6,282,438 B1 | * | 8/2001 | Maki et al. .................. | 356/342 |
| 6,289,230 B1 | * | 9/2001 | Chaiken et al. ............. | 600/322 |
| 6,374,128 B1 | * | 4/2002 | Toida et al. ................ | 356/319 |
| 6,424,858 B1 | * | 7/2002 | Williams ..................... | 600/473 |
| 6,438,396 B1 | * | 8/2002 | Cook et al. .................. | 600/310 |

OTHER PUBLICATIONS

No English Translation Provided.
Medical Society Journal of Japan, BME vol. 8, No. 5, pp. 41–50, 1994.

* cited by examiner

Primary Examiner—Marvin M. Lateef
Assistant Examiner—Eleni Mantis Mercader
(74) Attorney, Agent, or Firm—Sughrue Mion, PLLC

(57) ABSTRACT

A first measuring light beam of wavelength $\lambda_1$ equal to a wavelength at the isosbestic point between oxyhemoglobin and deoxyhemoglobin and a second measuring light beam of wavelength $\lambda_2$ differing from the first measuring light beam are incident on the same part of a subject such as a human finger and scan the subject by using an X–Y stage movable in X and Y directions. The first measuring light beam branches into two light beams. One of the two light beams is subjected to a frequency shift by a frequency shifter, while the other is transmitted through the subject. Thereafter, the two light beams are synthesized and a beat component of the synthesized first measuring light beam is detected by a first signal detection section. The first signal detection section outputs a first beat-component detection signal. For the second measuring light beam, a second beat-component detection signal is output in the same manner as the first measuring light beam. A personal computer generates an image signal based on a value of the second beat-component detection signal normalized by the first beat-component detection signal.

16 Claims, 3 Drawing Sheets

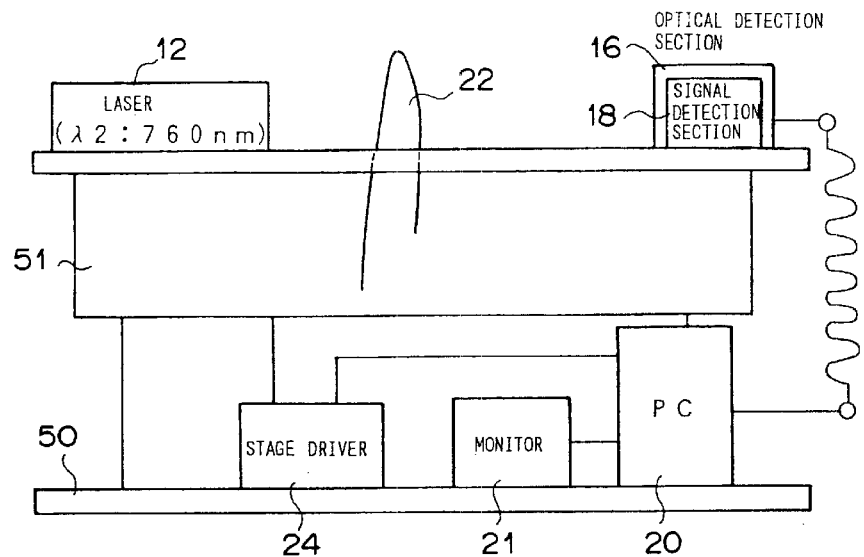
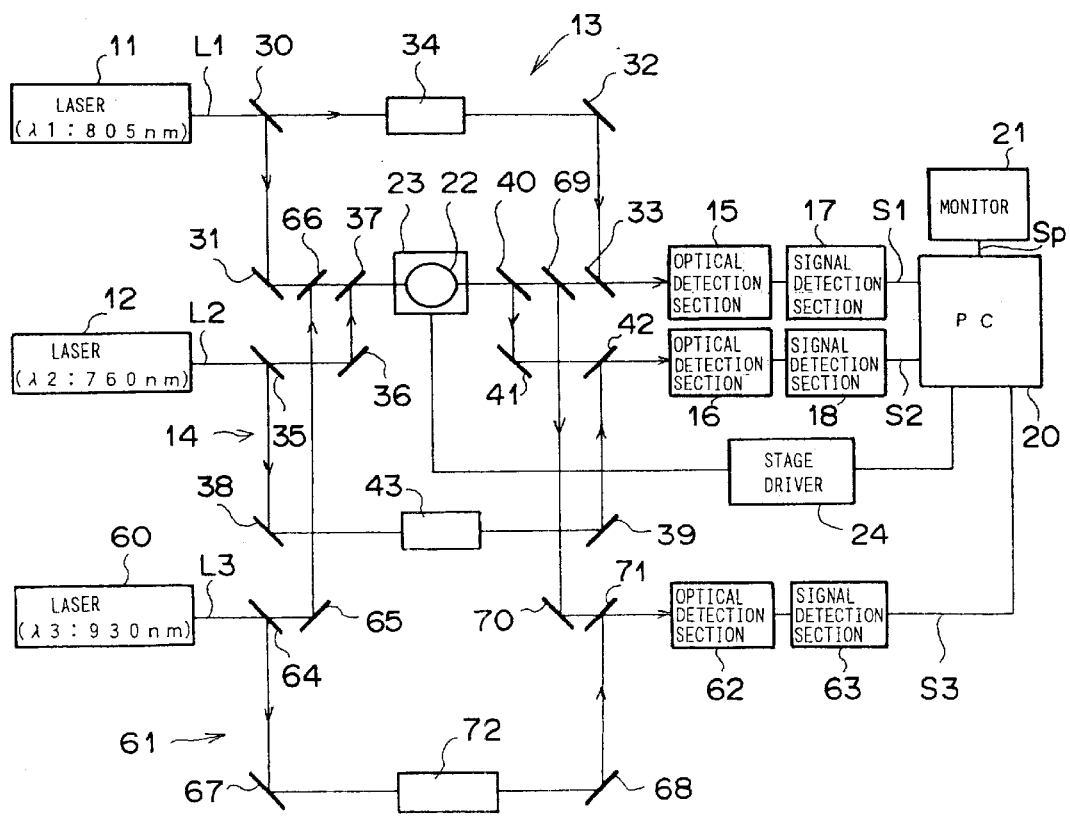

APPARATUS FOR IMAGING A BLOOD VESSEL

BACKGROUND OF THE INVENTION

1. Field of the Invention

The present invention relates generally to an apparatus for imaging and displaying a blood vessel, and more particularly to an apparatus for imaging and distinguishing an artery from a vein or vice versa.

2. Description of the Related Art

In clinical diagnosis, there have been wide demands for imaging and discriminating an artery from a vein or vice versa. For example, arteriosclerosis generally arises from a peripheral portion. Therefore, if the inside diameter image of the artery in this peripheral portion can be discriminated from a venous image and imaged, it can be utilized as diagnostic information with respect to arteriosclerosis.

As an apparatus for imaging and displaying a blood vessel, an X-ray blood vessel contrast photographing apparatus has hitherto been widely known. However, this X-ray blood vessel contrast photographing places a great burden on a subject and the execution thereof usually requires admission to a hospital, so there is a problem that it is difficult to easily perform the X-ray blood vessel contrast photographing on an outpatient.

In contrast to this, a technique of imaging a part of a living organism by light fluoroscopy has also been proposed as indicated in Medical Society Journal of Japan, BME Vol. 8, No. 5, 1994, pp. 41–50. In this imaging technique by light fluoroscopy, however, it is extremely difficult to clearly image and distinguish an artery-from a vein or vice versa.

SUMMARY OF THE INVENTION

The present invention has been made in view of the aforementioned circumstances. Accordingly, it is an object of the present invention to provide an apparatus which places a lower burden on a subject and is capable of imaging and distinguishing an artery from a vein or vice versa.

A blood vessel imaging apparatus according to the present invention applies optical heterodyne detection to imaging such that high space resolution is ensured with respect to a living organism which is a scattering medium, and distinguishes an artery and vein by taking advantage of a difference in light absorption characteristic between oxyhemoglobin and deoxyhemoglobin in the blood.

More specifically, the blood vessel imaging apparatus according to the present invention comprises:

light source means for emitting a first measuring light beam and a second measuring light beam differing from the first measuring light beam, the first measuring light beam having a wavelength equal to a wavelength at an isosbestic point between oxyhemoglobin and deoxyhemoglobin in the blood of a living organism;

an incident optics system for causing the first measuring light beam and the second measuring light beam to be incident on the same part of the living organism;

scanner means for scanning the living organism with the first measuring light beam and the second measuring light beam;

a first optical heterodyne detection system equipped with a first optics system for synthesizing the first measuring light beam and a branched first measuring light beam transmitted through the living organism; a first frequency shifter for giving a difference in frequency between the first measuring light beam and the branched first measuring light beam; and first detection means for detecting a first beat component of the synthesized first measuring light beam and outputting a first beat component detection signal;

a second optical heterodyne detection system equipped with a second optics system for synthesizing the second measuring light beam and a branched second measuring light beam transmitted through the living organism; a second frequency shifter for giving a difference in frequency between the second measuring light beam and the branched second measuring light beam; and second detection means for detecting a second beat component of the synthesized second measuring light beam and outputting a second beat component detection signal; and image signal generation means for generating an image signal, based on a value of the second beat component detection signal normalized by the first beat component detection signal.

In a preferred form of the present invention, the light source means emits a light beam of wavelength $\lambda_1$ as the first measuring light beam and emits a light beam of wavelength $\lambda_2$ as the second measuring light beam, and when it is assumed that a value of a beat component detection signal related to the measuring light beam of wavelength $\lambda_1$ is $I\lambda_1$ and a beat component detection signal related to the measuring light beam of wavelength $\lambda_2$ is $I\lambda_2$, the image signal generation means generates the image signal, based on a value of $\log(I\lambda_2/I\lambda_1)$.

The wavelength $\lambda_1$ of the first measuring light beam may be 805 nm and the wavelength $\lambda_2$ of the second measuring light beam may be 760 nm. Also, the wavelength $\lambda_1$ may be 805 nm and the wavelength $\lambda_2$ may be 930 nm.

In another preferred form of the present invention, the light source means emits a light beam of wavelength $\lambda_1$ as the first measuring light-beam and emits a light beam of wavelength $\lambda_2$ and a light beam of wavelength $\lambda_3$ as the second measuring light beam, and when a value of a beat component detection signal related to the measuring light beam of wavelength $\lambda_1$ is assumed to be $I\lambda_1$, a beat component detection signal related to the measuring light beam of wavelength $\lambda_2$ to be $I\lambda_2$, and a beat component detection signal related to the measuring light beam of wavelength $\lambda_3$ to be $I\lambda_3$, the image signal generation means generates the image signal, based on a difference between a value of $\log(I\lambda_2/I\lambda_1)$ and a value of $\log(I\lambda_3/I\lambda_1)$.

In the case of employing three kinds of measuring light beams, as described above, the wavelengths $\lambda_1$, wavelength $\lambda_2$, and the wavelength $\lambda_3$ are, for example, 805 nm, 760 nm, and 930 nm.

In still another preferred form of the present invention, the blood vessel imaging apparatus according to the present invention further comprises synchronous detection means for detecting a pulse wave of the artery of the living organism and performing the beat component detection of the first and second measuring light beams in synchronization with a predetermined phase of the pulse wave.

The arterial blood of a living organism includes oxyhemoglobin dominantly, while the venous blood includes deoxyhemoglobin dominantly. FIG. 6 shows the absorption spectra of oxyhemoglobin and deoxyhemoglobin that are light-absorbing materials, along with the spectrum of water that determines the optical characteristics of the tissues of the human body. As shown in the figure, the spectrum of oxyhemoglobin has a characteristic of low absorption on the short wavelength side of the isosbestic point (wavelength 805 nm), while the spectrum of deoxyhemoglobin has a characteristic of low absorption on the long wavelength side of the isosbestic point.

On the other hand, the beat component detection signals, output by the above-mentioned first and second optical heterodyne detection systems, indicate the intensities of only the straight light portion transmitted through the living organism and the scattered light portion close thereto, excluding the influence of scattering of the living organism that is a scattering medium. The value of the beat component detection signal will become greater if absorption of the measuring light beam is less.

Hence, in consideration of the absorption spectra of FIG. 6, consider the case of using a light beam of wavelength $\lambda_1$=805 nm equal to the isosbestic point wavelength as the first measuring light beam and using, for example, a light beam of $\lambda_2$=760 nm (where the absorption of deoxyhemoglobin is particularly greater with respect to the absorption of oxyhemoglobin) as the second measuring light beam.

If, in the above case, the first and second measuring light beams are transmitted through the venous part in which deoxyhemoglobin is dominantly included, the second beat component detection signal that is output by the second optical heterodyne detection system basically indicates a lesser value because absorption is greater, as compared with the first beat component detection signal that is output by the first optical heterodyne detection system. If, on the other hand, the first and second measuring light beams are transmitted through the arterial part in which oxyhemoglobin is dominantly included, the second beat component detection signal that is output by the second optical heterodyne detection system basically indicates a greater value because absorption is less, as compared with the first beat component detection signal that is output by the first optical heterodyne detection system.

The beat component detection signals that are output by the first and second optical heterodyne detection systems are influenced by light attenuation (absorption and scattering) due to soft tissues or bones other than blood and a change in the amount of blood. However, if the second beat component detection signal output by the second optical heterodyne detection system is normalized based on the first beat component detection signal output by the first optical heterodyne detection system, the normalized value will exclude these major causes of change and accurately indicate a relation in magnitude between both signals based on the above-mentioned difference in absorption characteristic.

Therefore, by generating an image signal on the basis of the aforementioned normalized value, either the arterial part alone or the venous part alone can be imaged. That is, for example, when the values of the first and second beat component detection signals of the first and second optical heterodyne detection systems are assumed to be $I\lambda_1$ and $I\lambda_2$, respectively, the value ($I\lambda_2/I\lambda_1$) of the latter normalized by the former will assume a value greater than 1 if the first and second measuring light beams are transmitted through the arterial part and assume a value less than 1 if the first and second measuring light beams are transmitted through the venous part.

Hence, if only a positive value of $\log(I\lambda_2/I\lambda_1)$, obtained for each scanning position by scanning the living organism with the first and second measuring light beams, is converted to an image signal and an image is reproduced by the image signal, then the image will show the arterial part alone. If, on the other hand, only a negative value of $\log(I\lambda_2/I\lambda_1)$ obtained for each scanning position is converted to an image signal and an image is reproduced by the image signal, then the image will show the venous part alone.

It is also possible to image either the arterial part alone or the venous part alone, based on the relation in magnitude between the aforementioned normalized value ($I\lambda_2/I\lambda_1$) and threshold value=1.

On the other hand, assume that the beat component detection signal related to the measuring light beam of wavelength $\lambda_1$ is $I\lambda_1$, the beat component detection signal related to the measuring light beam of wavelength $\lambda_2$ is $I\lambda_2$, and the beat component detection signal related to the measuring light beam of wavelength $\lambda_3$ is $I\lambda_3$. When an image signal is generated based on the difference between a value of $\log(I\lambda_2/I\lambda_1)$ and a value of $\log(I\lambda_3/I\lambda_1)$, the advantage that the absolute value of the signal becomes greater according to the difference is obtained, as compared with the case of generating an image signal on the basis of either only a value of $\log(I\lambda_2/I\lambda_1)$ or only a value of $\log(I\lambda_3/I\lambda_1)$.

BRIEF DESCRIPTION OF THE DRAWINGS

The above and other objects and advantages will become apparent from the following detailed description when read in conjunction with the accompanying drawings wherein:

FIG. 3 is a side view showing the blood vessel imaging apparatus according to the second embodiment of the present invention;

FIG. 4 is a schematic block diagram showing a blood vessel imaging apparatus according to a third embodiment of the present invention;

DESCRIPTION OF THE PREFERRED EMBODIMENTS

Embodiments of the present invention will hereinafter be described with reference to the drawings.

Figure 1:
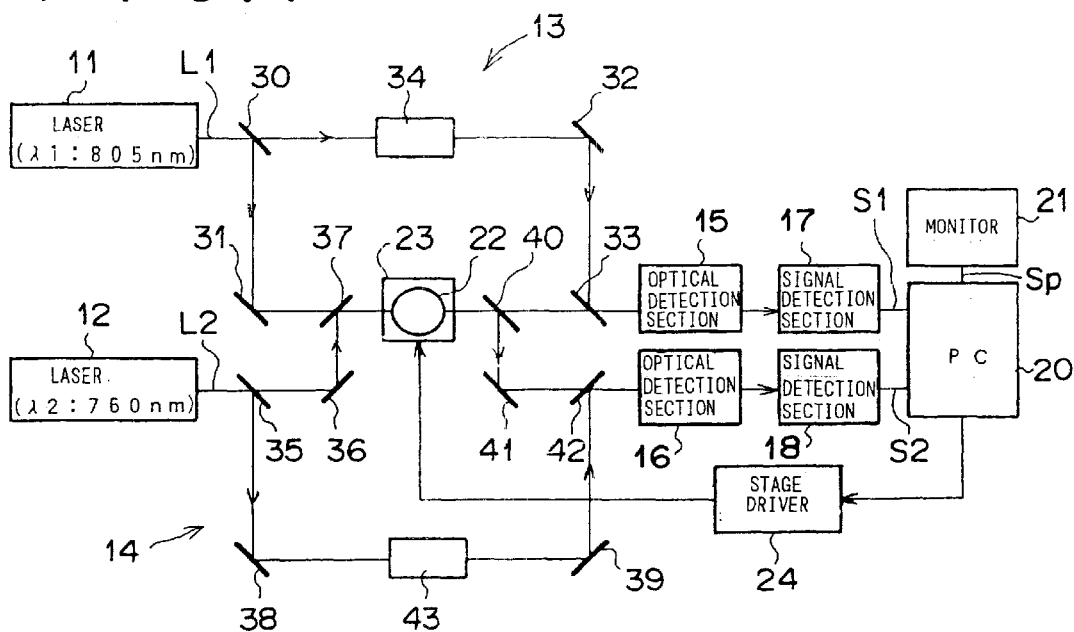
FIG. 1 is a schematic block diagram showing a blood vessel imaging apparatus according to a first embodiment of the present invention.

FIG. 1 schematically illustrates a blood vessel imaging apparatus according to a first embodiment of the present invention. The apparatus according to the first embodiment includes: a first laser 11 for emitting a first measuring light beam L1 of wavelength $\lambda_1$=805 nm; a second laser 12 for emitting a second measuring light beam L2 of wavelength $\lambda_2$=760 nm differing from the first measuring light beam L1; a first optics system 13 for the first measuring light beam L1; a second optics system 14 for the second measuring light beam L2; a first photo detector 15 for receiving the first measuring light beam L1 emitted from the first optics system 13; a second photo detector 16 for receiving the second measuring light beam L2 emitted from the second optics system 14; a first signal detection section 17 connected to the first photo detector, 15 for detecting a first beat component included as described infra in the first measuring light beam L1; and a second signal detection section 18 connected to the second photo detector 16 for detecting a second beat component included as described infra in the second measuring light beam L2.

This imaging apparatus further includes a personal computer (image signal generation means) 20 for receiving outputs of the first signal detection section 17 and the second signal detection section 18 and an image monitor (e.g., a CRT display, etc.) 21 connected to the personal computer 20.

Furthermore, an X–Y stage 23 movable in a two-dimensional direction is provided for placing a subject (e.g., a human finger, etc.) 22 that is a blood-vessel imaging object. This X-Y stage 23 is driven by a stage driver 24, the operation of the stage driver 24 being controlled by the personal computer 20.

Figure 6:
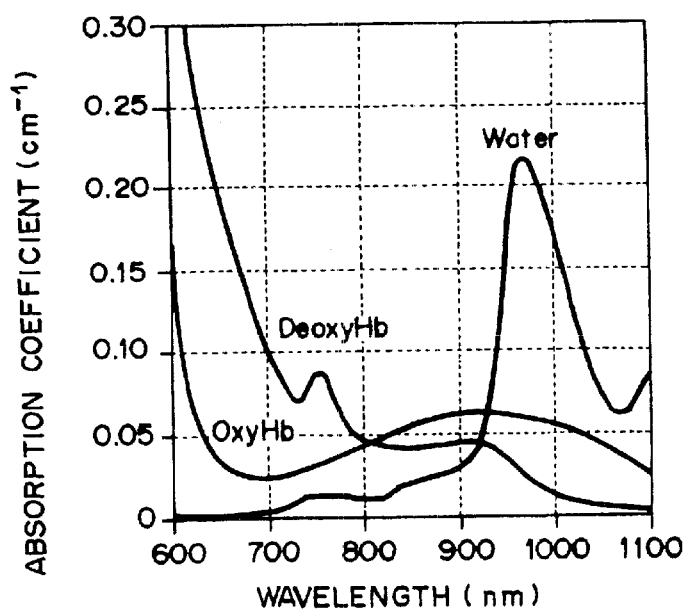
FIG. 6 is a graph showing the absorption spectra of oxyhemoglobin, deoxyhemoglobin, and water.

Note that the aforementioned wavelength $\lambda_1$=805 nm is a wavelength at the isosbestic point between the oxyhemoglobin and deoxyhemoglobin in the blood of a human body, as described above with reference to FIG. 6. On the other hand, the wavelength $\lambda_2$=760 nm is a wavelength at which absorption of deoxyhemoglobin becomes significantly greater with respect to absorption of oxyhemoglobin.

The first optics system 13, which constitutes a first optical heterodyne detection system along with the first photo detector 15 and the first signal detection section 17, comprises a half mirror 30 for branching the first measuring light beam L1 emitted from the first laser 11 into two light beams; a mirror 31 for reflecting the first measuring light beam L1 reflected and branched by the half mirror 30 and directing the reflect first measuring light beam L1 to the subject 22; a mirror 32 for reflecting the first measuring light beam L1 transmitted through the half mirror 30; and a half mirror 33 for synthesizing the first measuring light beam L1 reflected by the mirror 32 with the first measuring light beam L1 transmitted through the subject 22.

Furthermore, a first frequency shifter 34 (e.g., an AOM) for applying a predetermined frequency shift in the order of tens of MHz on the measuring light beam L1 is inserted into the optical path of the first measuring light beam L1 transmitted through the half mirror 30.

On the other hand, the second optics system 14, which constitutes a second optical heterodyne detection system along with the second photo detector 16 and the second signal detection section 18, comprises a half mirror 35 for branching the second measuring light beam L2 emitted from the second laser 12 into two light beams; a mirror 36 for reflecting the second measuring light beam L2 transmitted through the half mirror 35; a dichroic mirror 37 for reflecting the second measuring light beam L2 reflected by the mirror 36 and also transmitting the first measuring light beam L1 therethrough so that both are incident on the subject 22 along the same optical path; mirrors 38 and 39 for reflecting in sequence the second measuring light beam L2 reflected and branched by the half mirror 35; a dichroic mirror 40 for reflecting the first measuring light beam L1 transmitted through the subject 22 and transmitting the second measuring light beam L2 therethrough and thereby separating both; a mirror 41 for reflecting the second measuring light beam L2 reflected by the dichroic mirror 40; and a half mirror 42 for synthesizing the second measuring light beam L2 reflected by the mirror 41 with the second measuring light beam L2 reflected by the mirror 39.

Furthermore, a second frequency shifter 43 (e.g., an AOM) for subjecting the second measuring light beam L2 to a predetermined frequency shift in the order of tens of MHz is inserted into the optical path of the second measuring light beam L2 between the mirror 38 and the mirror 39.

Note that the half mirror 30 and mirror 31 of the first optics system 13 and the half mirror 35, mirror 36, and dichroic mirror 37 of the second optics system 14 constitute an incident optics system for causing the first measuring light beam L1 and the second measuring light beam L2 to be incident on the same part of the subject 22.

A description will hereinafter be given of the operation of the apparatus of the first embodiment having the aforementioned construction. In obtaining the image of the blood vessel of the subject 22, the first measuring light beam L1 of wavelength $\lambda_1$=805 nm emitted from the first laser 11 and the second measuring light beam L2 of wavelength $\lambda_2$=760 nm emitted from the second laser 12 are synthesized by the dichroic mirror 37, as described above, and are emitted to the same point of the subject 22. Simultaneously, the X–Y stage 23 is driven, whereby the first measuring light beam L1 and the second measuring light beam L2 scan the subject 22 two-dimensionally.

If the first measuring light beam L1 transmitted through the subject 22 and the first measuring light beam L1 subjected to a frequency shift by the first frequency shifter 34 are synthesized by the half mirror 33, the synthesized first measuring light beam L1 will include a beat component of the same frequency as the shifted frequency. The output of the first photo detector 15 that receives the synthesized first measuring light beam L1 is input to the first signal detection section 17, which consists, for example, of a band pass filter and a level measuring unit. In the first signal detection section 17, the aforementioned beat component is detected and converted to a first electric beat signal S1.

The first beat signal S1 output by the first signal detection section 17 indicates the intensities of only the straight component of the first measuring light beam L1 transmitted through the subject 22, which is a scattering medium, and the scattered component close thereto. Therefore, if an image related to the subject 22 is obtained based on this first beat signal S1, high space resolution will be ensured, although the first measuring light beam L1 scatters at the subject 22.

The foregoing description is also true of the second measuring light beam L2. That is, if the second measuring light beam L2 transmitted through the subject 22 and the second measuring light beam L2 subjected to a frequency shift by the second frequency shifter 43 are synthesized by the half mirror 42, the synthesized second measuring light beam L2 will include the beat component of the same frequency as the shifted frequency. The output of the second photo detector 16 that receives the synthesized second measuring light beam L2 is input to the second signal detection section 18, which consists, for example, of a band pass filter and a level measuring unit. In the second signal detection section 18, the aforementioned beat component is detected and converted to a second electric beat signal S2.

The second beat signal S2 output by the second signal detection section 18 indicates the intensities of only the straight component of the second measuring light beam L2 transmitted through the subject 22, which is a scattering medium, and the scattered component close thereto. Therefore, if an image related to the subject 22 is obtained based on this second beat signal S2, high space resolution will be ensured, although the second measuring light beam L2 scatters at the subject 22.

Thus, the first signal detection section 17 and the second signal detection section 18 output the first and second beat signals S1 and S2, respectively, for each scanning position on the subject 22 when the subject 22 is scanned with the first measuring light beam L1 and the second measuring light beam L2 in the aforementioned manner.

These beat signals S1 and S2 are input to the aforementioned personal computer 20. When the values of the beat signals S1 and S2 are assumed to be $I\lambda_1$ and $I\lambda_2$, the personal computer 20 calculates the logarithmic value of the latter normalized by the former, that is, $\log(I\lambda_2/I\lambda_1)$.

When the value of $\log(I\lambda_2/I\lambda_1)$ calculated for each two-dimensional scanning position on the subject 22 is positive, the personal computer 20 converts it to an image signal $S_P$ having a value corresponding to the absolute value of $\log(I\lambda_2/\lambda_1)$ and inputs the image signal $S_P$ to the image monitor 21. Note that when the value of $\log(I\lambda_2/I\lambda_1)$ calculated for each two-dimensional scanning position on the subject 22 is zero or negative, the personal computer 20 automatically converts it to an image signal $S_P$ having a uniform value (e.g., a value carrying the lowest density value) independently of the value of $\log(I\lambda_2/I\lambda_1)$.

In the image monitor 21, a two-dimensional image is reproduced and displayed, based on the image signal $S_P$ generated in the aforementioned manner. This image becomes an arterial image showing only the arterial part, excluding the venous part of the subject 22. The reason for this is as described in detail with reference to FIG. 6.

If, on the other hand, only a negative value of $\log(I\lambda_2/I\lambda_1)$ calculated for each two-dimensional scanning position on the subject 22 is converted to an image signal $S_P$ and an image is reproduced based on the image signal $S_P$, then the image will become the venous image of the subject 22.

Figure 2:
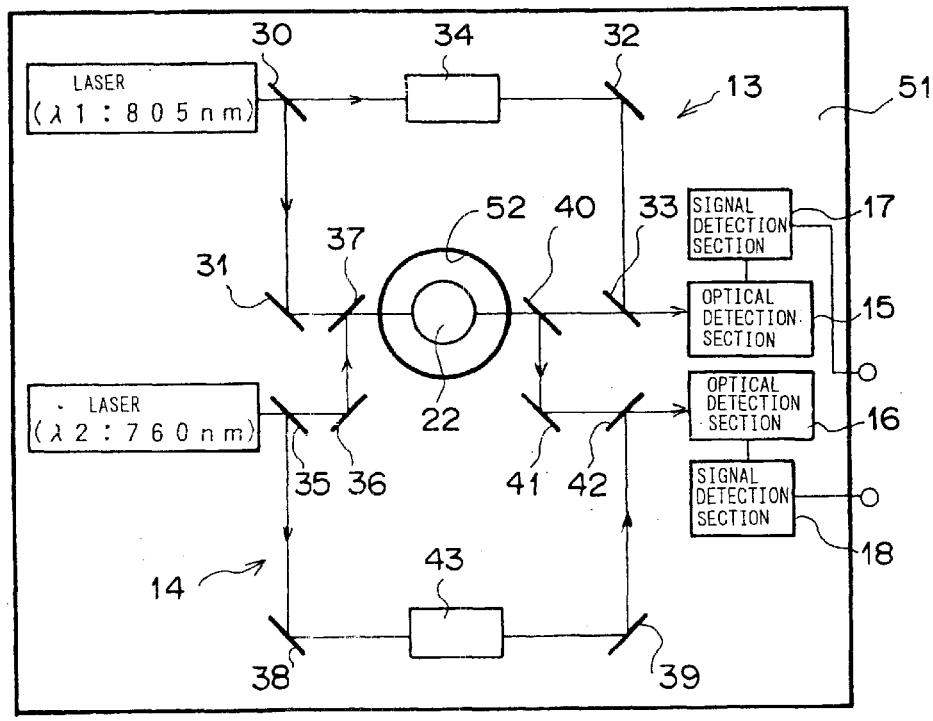
FIG. 2 is a top view showing a blood vessel imaging apparatus according to a second embodiment of the present invention.

Now, a description will be given of a second embodiment of the present invention. FIGS. 2 and 3 show top and side views of a blood vessel imaging apparatus according to the second embodiment of the present invention, respectively. Note that in these figures, the same reference numerals will be applied to the same components as those in FIG. 1 and a description thereof is omitted unless it is particularly needed (the same shall apply hereinafter).

In the apparatus of the second embodiment, the same personal computer 20, image monitor 21, and stage driver 24 as those shown in FIG. 1 are mounted on a base 50 and the other components are all mounted on an X–Z stage 51. This X–Z stage 51 is movable in X and Z directions, that is, a right-and-left direction and an up-and-down direction in FIG. 3, the central portion being provided with an opening 52, as shown in FIG. 2.

For instance, a subject 22 such as a human finger is disposed within the opening 52 of the aforementioned X–Z stage 51 when the artery is imaged. This stage X–Z stage 51 is driven to move in the X and Z directions by the stage driver 24, whereby the subject 22 is scanned two-dimensionally with a first measuring light beam L1 and a second measuring light beam L2. The remaining construction is basically the same as the first embodiment.

Now, a description will be given of a third embodiment of the present invention. FIG. 4 schematically illustrates a blood vessel imaging apparatus according to the third embodiment of the present invention. The apparatus of FIG. 4 basically differs from the apparatus of FIG. 1 in that the second optical heterodyne detection system prescribed in the present invention and components related thereto are further provided.

That is, in addition to the construction of FIG. 1, the apparatus of the third embodiment is further provided with a third laser 60 for emitting a third measuring light beam L3 of wavelength $I\lambda_3=930$ nm, a third optics system 61 for the third measuring light beam L3, a third photo detector 62 for receiving the third measuring light beam L3 emitted from the third optics system 61, and a third signal detection section 63 connected to the third photo detector 62 for detecting a beat component included as described below in the third measuring light beam L3. A third beat signal S3 output by the third signal detection section 63 is input to the aforementioned personal computer 20 along with the first and second beat signals S1 and S2.

On the other hand, the third optics system 61 comprises a half mirror 64 for branching the third measuring light beam L3 emitted from the third laser 60 into two light beams; a mirror 65 for reflecting the third measuring light beam L3 transmitted through the half mirror 64; a dichroic mirror 66 for reflecting the third measuring light beam L3 reflected by the mirror 65 and also transmitting the first measuring light beam L1 therethrough so that both are incident on the subject 22 along the same optical path; mirrors 67 and 68 for reflecting in sequence the third measuring light beam L3 reflected and branched by the half mirror 64; a dichroic mirror 69 for reflecting the third measuring light beam L3 transmitted through the subject 22 and transmitting the first measuring light beam L1 therethrough and thereby separating both; a mirror 70 for reflecting the third measuring light beam L3 reflected by the dichroic mirror 69; and a half mirror 42 for synthesizing the third measuring light beam L3 reflected by the mirror 70 with the third measuring light beam L3 reflected by the mirror 68.

Furthermore, a third frequency shifter 72 (e.g., an AOM) for subjecting the third measuring light beam L3 to a predetermined frequency shift in the order of tens of MHz is inserted into the optical path of the third measuring light beam L3 between the aforementioned mirror 67 and mirror 68.

Similarly, if the third measuring light beam L3 transmitted through the subject 22 and the third measuring light beam L3 subjected to a frequency shift by the third frequency shifter 72 are synthesized by the half mirror 71, the synthesized third measuring light beam L3 will include a beat component of the same frequency as the shifted frequency. The output of the third photo detector 62 that receives the synthesized third measuring light beam L3 is input to the third signal detection section 63, which consists, for example, of a band pass filter and a level measuring unit. In the third signal detection section 63, the aforementioned beat component is detected and converted to a third electric beat signal S3.

Thus, the first signal detection section 17, the second signal detection section 18, and the third signal detection section 63 output the first, second and third beat signals S1, S2, and S3, respectively, for each scanning position on the subject 22 when the subject 22 is scanned with the first measuring light beam L1, the second measuring light beam L2, and the third measuring light beam L3 in the aforementioned manner.

These beat signals S1, S2, and S3 are input to a personal computer 20. When the values of the beat signals S1, S2, and S3 are assumed to be $I\lambda_1$, $I\lambda_2$, and $I\lambda_3$, the personal computer 20 calculates $\log(I\lambda_2/I\lambda_1)-\log(I\lambda_3/I\lambda_1)$.

The personal computer 20 converts only a positive value of $\log(I\lambda_2/I\lambda_1)-\log(I\lambda_3/I\lambda_1)$, calculated for each two-dimensional scanning position on the subject 22, to an image signal $S_P$ having a value corresponding to the absolute value of $\log(I\lambda_2/I\lambda_1)-\log(I\lambda_3/I\lambda_1)$ and inputs the image signal $S_P$ to an image monitor 21. Note that when the value of $\log(I\lambda_2/I\lambda_1)-\log(I\lambda_3/I\lambda_1)$ calculated for each two-dimensional scanning position on the subject 22 is zero or negative, the personal computer 20 automatically converts it to an image signal $S_P$ having a uniform value (e.g., a value carrying the lowest density value) independently of the value of $\log(I\lambda_2/I\lambda_1)-\log(I\lambda_3/I\lambda_1)$.

In the image monitor 21, a two-dimensional image is reproduced and displayed, based on the image signal $S_P$ generated in the aforementioned manner. This image becomes an arterial image showing only the arterial part, excluding the venous part of the subject 22. Since a negative value of $\log(I\lambda_3/I\lambda_1)$ is subtracted, the apparatus according to the third embodiment is capable of assuming a greater absolute value of the signal, compared with the case of generating the image signal $S_P$ from a value of $\log(I\lambda_2/I\lambda_1)$.

If, on the other hand, only a negative value of $\log(I\lambda_2/I\lambda_1) - \log(I\lambda_3/I\lambda_1)$ calculated for each two-dimensional scanning position on the subject 22 is converted to an image signal $S_P$ and an image is reproduced based on the image signal $S_P$ then the image will become the venous image of the subject 22.

Figure 5:
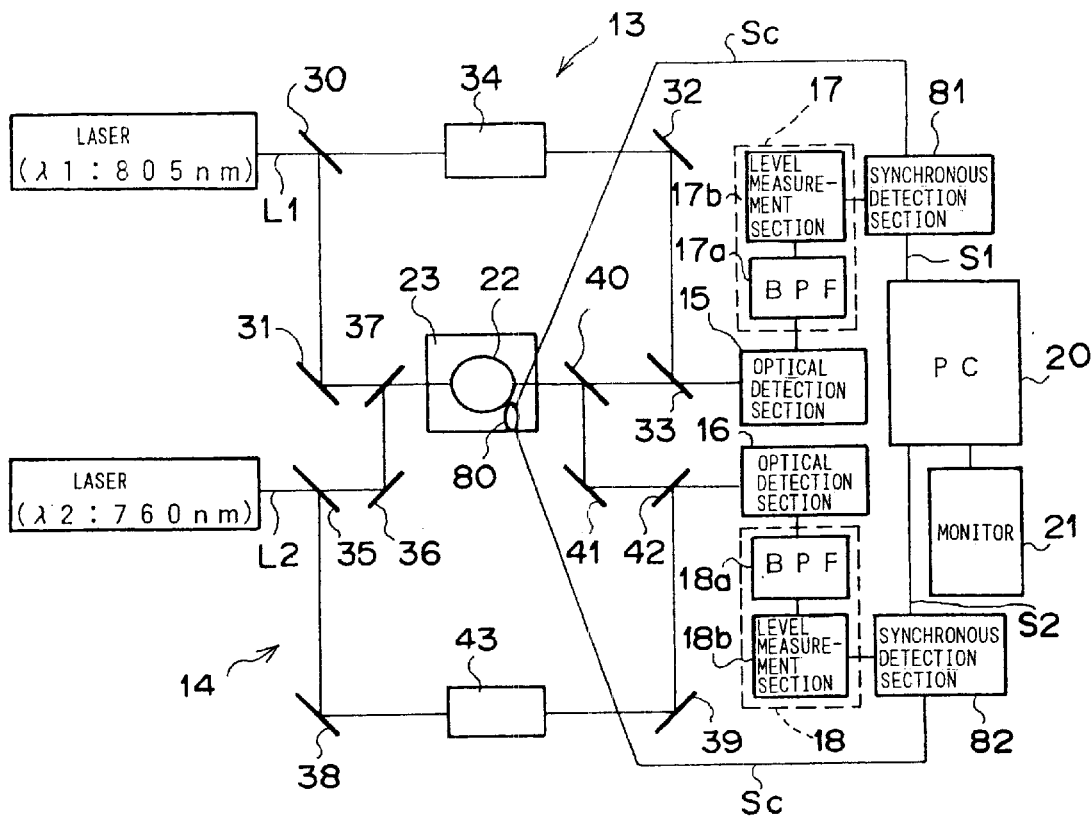
FIG. 5 is a schematic block diagram showing a blood vessel imaging apparatus according to a fourth embodiment of the present invention.

Now, a description will be given of a fourth embodiment of the present invention. FIG. 5 schematically illustrates a blood vessel imaging apparatus according to the fourth embodiment of the present invention. The apparatus of FIG. 5 basically differs from the apparatus of FIG. 1 in that the construction for detecting beat signals S1 and S2 in Synchronization with the pulse wave of the subject 22 is added.

That is, in addition to the construction of FIG. 1, the apparatus of the fourth embodiment is provided with a pulse-wave signal detection section 80 for detecting the pulse wave of the subject 22; a first synchronous detection section 81 for sampling the beat signal S1 output by a first signal detection section 17, based on a pulse wave signal $S_c$ from the pulse—wave signal detection section 80; and a second synchronous detection section 82 for sampling the beat signal S2 output by a second signal detection section 18, based on a pulse wave signal $S_c$ from the pulse-wave signal detection section 80.

Note that in the fourth embodiment, the first signal detection section 17 comprises a band pass filter 17a and a level measurement section 17b. Similarly, the second signal detection section 18 comprises a band pass filter 18a and a level measurement section 18b.

Each of the aforementioned samplings is executed in synchronization with the peak or bottom of the pulse wave of the subject 22 indicated by the pulse wave signal $S_c$. If the blood vessel is imaged taking advantage of the beat signals S1 and S2 thus detected in synchronization with the pulse wave, accurate arterial and venous images can be obtained without being influenced by a change in the blood vessel diameter due to pulsation. Furthermore, signal attenuation due to tissues other than blood can be corrected.

Although the apparatuses described in detail above have been found to be most satisfactory and preferred, many variations in structure are possible. Because many variations and different embodiments may be made within the scope of the inventive concept herein taught, it should be understood that the details herein are to be interpreted as illustrative and not in a limiting sense.

What is claimed is:

1. A blood vessel imaging apparatus comprising:
   light source means for emitting a first measuring light beam and a second measuring light beam differing from said first measuring light beam, said first measuring light beam having a wavelength equal to a wavelength at an isosbestic point between oxyhemoglobin and deoxyhemoglobin in the blood of a living organism;
   an incident optics system for causing said first measuring light beam and said second measuring light beam to be incident on the same part of said living organism;
   scanner means for scanning said living organism with said first measuring light beam and said second measuring light beam;
   a first optical heterodyne detection system equipped with a first optics system for synthesizing said first measuring light beam and a branched first measuring light beam transmitted through said living organism; a first frequency shifter for giving a difference in frequency between said first measuring light beam and said branched first measuring light beam; and first detection means for detecting a first beat component of said synthesized first measuring light beam and outputting a first beat component detection signal;
   a second optical heterodyne detection system equipped with a second optics system for synthesizing said second measuring light beam and a branched second measuring light beam transmitted through said living organism; a second frequency shifter for giving a difference in frequency between said second measuring light beam and said branched second measuring light beam; and second detection means for detecting a second beat component of said synthesized second measuring light beam and outputting a second beat component detection signal; and
   image signal generation means for generating an image signal, based on a value of said second beat component detection signal normalized by said first beat component detection signal.

2. The blood vessel imaging apparatus as set forth in claim 1, wherein
   said light source means emits a light beam of wavelength $\lambda_1$ as said first measuring light beam and emits a light beam of wavelength $\lambda_2$ as said second measuring light beam; and
   when it is assumed that a value of a beat component detection signal related to said measuring light beam of wavelength $\lambda_1$ is $I\lambda_1$ and a beat component detection signal related to said measuring light beam of wavelength $\lambda_2$ is $I\lambda_2$, said image signal generation means generates said image signal, based on a value of $\log(I\lambda_2/I\lambda_1)$.

3. The blood vessel imaging apparatus as set forth in claim 2, wherein said wavelength $\lambda_1$ is 805 nm and said wavelength $\lambda_2$ is 760 nm.

4. The blood vessel imaging apparatus as set forth in claim 2, wherein said wavelength $\lambda_1$ is 805 nm and said wavelength $\lambda_2$ is 930 nm.

5. The blood vessel imaging apparatus as set forth in claim 1, wherein
   said light source means emits a light beam of wavelength $\lambda_1$ as said first measuring light beam and emits a light beam of wavelength $\lambda_2$ and a light beam of wavelength $\lambda_3$ as said second measuring light beam; and
   when a value of a beat component detection signal related to said measuring light beam of wavelength $\lambda_1$ is assumed to be $I\lambda_1$, a beat component detection signal related to said measuring light beam of wavelength $\lambda_2$ to be $I\lambda_2$, and a beat component detection signal related to said measuring light beam of wavelength $\lambda_3$ to be $I\lambda_3$, said image signal generation means generates said image signal, based on a difference between a value of $\log(I\lambda_2/I\lambda_1)$ and a value of $\log(I\lambda_3/I\lambda_1)$.

6. The blood vessel imaging apparatus as set forth in claim 5, wherein said wavelength $\lambda_1$ is 805 nm, said wavelength $\lambda_2$ is 760 nm, and said wavelength $\lambda_3$ is 930 nm.

7. The blood vessel imaging apparatus as set forth in claim 1, further comprising synchronous detection means for detecting a pulse wave of the artery of said living organism and performing the beat component detection of said first and second measuring light beams in synchronization with a predetermined phase of said pulse wave.

8. The blood vessel imaging apparatus as set forth in claim 2, further comprising synchronous detection means for detecting a pulse wave of the artery of said living organism and performing the beat component detection of said first and second measuring light beams in synchronization with a predetermined phase of said pulse wave.

9. The blood vessel imaging apparatus as set forth in claim 3, further comprising synchronous detection means for detecting a pulse wave of the artery of said living organism and performing the beat component detection of said first and second measuring light beams in synchronization with a predetermined phase of said pulse wave.

10. The blood vessel imaging apparatus as set forth in claim 4, further comprising synchronous detection means for detecting a pulse wave of the artery of said living organism and performing the beat component detection of said first and second measuring light beams in synchronization with a predetermined phase of said pulse wave.

11. The blood vessel imaging apparatus as set forth in claim 5, further comprising synchronous detection means for detecting a pulse wave of the artery of said living organism and performing the beat component detection of said first and second measuring light beams in synchronization with a predetermined phase of said pulse wave.

12. The blood vessel imaging apparatus as set forth in claim 6, further comprising synchronous detection means for detecting a pulse wave of the artery of said living organism and performing the beat component detection of said first and second measuring light beams in synchronization with a predetermined phase of said pulse wave.

13. The blood vessel imaging apparatus as set forth in claim 2, wherein if log $(I\lambda_2/I\lambda_1)$ is a positive value, said image signal generation means generates said image signal that produces an image showing an arterial part.

14. The blood vessel imaging apparatus as set forth in claim 2, wherein if log $(I\lambda_2/I\lambda_1)$ is a negative value, said image signal generation means generates said image signal that produces an image showing a venous part.

15. The blood vessel imaging apparatus as set forth in claim 1, wherein if said first measuring light beam and said second measuring light beam are transmitted through a venous part, a value of said second beat component detection signal decreases.

16. The blood vessel imaging apparatus as set forth in claim 1, wherein if said first measuring light beam and said second measuring light beam are transmitted through an arterial part, a value of said second beat component detection signal increases.

* * * * *